(12) United States Patent
Cannan et al.

(10) Patent No.: US 8,709,975 B2
(45) Date of Patent: Apr. 29, 2014

(54) AQUEOUS FLOWABLE CONCENTRATE COMPOSITIONS OF A MICROENCAPSULATED DINITROANILINE HERBICIDE

(75) Inventors: Terrance M. Cannan, Raleigh, NC (US); Paul Ch. Kierkus, Wake Forest, NC (US)

(73) Assignee: BASF SE, Ludwigshafen (DE)

( * ) Notice: Subject to any disclaimer, the term of this patent is extended or adjusted under 35 U.S.C. 154(b) by 6 days.

(21) Appl. No.: 13/140,047

(22) PCT Filed: Dec. 18, 2009

(86) PCT No.: PCT/EP2009/067520
§ 371 (c)(1),
(2), (4) Date: Jun. 16, 2011

(87) PCT Pub. No.: WO2010/070096
PCT Pub. Date: Jun. 24, 2010

(65) Prior Publication Data
US 2011/0251064 A1    Oct. 13, 2011

Related U.S. Application Data

(60) Provisional application No. 61/139,120, filed on Dec. 19, 2008.

(51) Int. Cl.
*A01N 25/26*    (2006.01)
*A01N 57/00*    (2006.01)

(52) U.S. Cl.
USPC ........................................... 504/100; 504/127

(58) Field of Classification Search
None
See application file for complete search history.

(56) References Cited

U.S. PATENT DOCUMENTS 5,705,174 A * 1/1998 Benoff et al. ................. 424/408
5,910,314 A   6/1999 Benoff et al.

FOREIGN PATENT DOCUMENTS

| EP | 0 619 073 | 10/1994 |
| EP | 619073 | * 10/1994 |
| WO | WO 00/30451 | 6/2000 |

\* cited by examiner

*Primary Examiner* — Alton Pryor
(74) *Attorney, Agent, or Firm* — Brinks Gilson & Lione

(57) ABSTRACT

The present invention relates to aqueous flowable concentrate compositions of a microencapsulated dinitroaniline herbicide, in particular pendimethalin, which are flowable and have improved storage stability. The compositions contain: i. 50 to 400 g/l of a dinitroaniline herbicide in the form of microcapsules comprising a core material containing the dinitroaniline herbicide, in particular pendimethalin, and a polymeric wall material, the microcapsules being dispersed in an aqueous phase; ii. 100 to 500 g/l of a glyphosate salt which is dissolved in the aqueous phase and iii. at least one anionic surface-active substance.

21 Claims, No Drawings

AQUEOUS FLOWABLE CONCENTRATE COMPOSITIONS OF A MICROENCAPSULATED DINITROANILINE HERBICIDE

This application is a National Stage application of International Application No. PCT/EP2009/067520, filed Dec. 18, 2009, which claims the benefit of U.S. Provisional Application No. 61/139,120, filed Dec. 19, 2008, the entire contents of which are hereby incorporated herein by reference.

The present invention relates to aqueous flowable concentrate compositions of a microencapsulated dinitroanline herbicide, in particular pendimethalin, which are flowable and have improved storage stability.

Water-insoluble pesticides are often formulated into aqueous suspension concentrates which are also referred to as aqueous flowables. Suspension concentrates are aqueous compositions containing the pesticide as fine particles which are dispersed in the aqueous medium. The concentration of the pesticide in such concentrates is usually higher than 10 g/l and mostly at least 50 g/l. Suspension concentrates have the desirable characteristics of a liquid that may be poured or pumped and which can easily be diluted with water to the desired concentration required for application. In contrast to emulsion concentrates the suspension concentrates have the added advantage of not requiring the use of water-immiscible organic solvents.

Problems, which are associated in general with suspension concentrates, are settling and caking resulting in the instability of the formulation, difficulty in processing and unreliability of its usage. These problems are pronounced in case of low-melting pesticides, such as dinitroaniline herbicides, in particular in case of pendimethalin (common name for N-(1-ethyl propyl)-2,6-dinitro-3,4-dimethyl anilin). A further problem associated with formulations of dinitroaniline herbicides, such pendimethalin results from the tendency of dinitroaniline herbicides to form large crystals upon aging resulting in an increased settling of the dinitroaniline herbicide particles and thus in an instability, difficulty in processing and unreliability of usage. These problems become most serious when storing aqueous suspension concentrates of dinitroaniline herbicides at temperatures above 35° C. and especially above 40° C.

It is principally known that the storage stability of a suspension concentrate of a water-insoluble active ingredient, which tends to separate from the from the formulation, can be increased by microencapsulation of the active ingredient, i.e. by providing a formulation, wherein the active ingredient is present in the form of microcapsule comprising a core material containing the active ingredient and a polymeric wall material surrounding the core material.

U.S. Pat. No. 5,705,174 and U.S. Pat. No. 5,910,314 describe aqueous flowable concentrate compositions of pendimethalin particles which are encapsulated by a polymeric wall material (micro-encapsulated pendimethalin), the concentrate composition further containing large amounts of an inorganic salt or salt mixture. The compositions are prepared by dispersing a water-insoluble solution of a reactive wall forming material and pendimethalin in an aqueous solution of the salt. The compositions show a reduced tendency to form large crystals and thus have good storage stability. The inventors of U.S. Pat. No. 5,705,174 and U.S. Pat. No. 5,910,314 believe that the salt reduces the solubility of the pendimethalin in the aqueous phase of the suspension and thereby reduces or eliminates the capability of pendimethalin to crystallize from the suspension. However, the large amount of inorganic salt in the formulation is not always acceptable.

Therefore, it is an object to provide aqueous formulations of dinitroaniline herbicides which are storage stable, even at elevated temperature, which have an acceptable viscosity, which have a good or superior herbicidal activity and avoid the necessity of large amounts of inorganic salts.

It was surprisingly found that these and further objects are solved by the flowable aqueous concentrate compositions as defined herein.

Therefore, the present invention relates to a flowable aqueous concentrate composition containing:
  i. 50 to 400 g/l of a dinitroaniline herbicide in the form of microcapsules comprising a core material containing the dinitroaniline herbicide, in particular pendimethalin, and a polymeric wall material, wherein the microcapsules are present in the form of an aqueous dispersion, containing the microcapsules dispersed in the aqueous phase of the dispersion;
  ii. 100 to 500 g/l of a glyphosate salt which is dissolved in the aqueous phase and
  iii. at least one anionic surface-active substance.

The glyphosate salt surprisingly imparts an increased stability to the composition of the microencapsulated dinitroaniline herbicide against leaching of the dinitroaniline herbicide from the microcapsules and thus increases the storage stability of an aqueous microcapsule composition containing a dinitroaniline herbicide in the form of microcapsules. This was rather surprising, since the addition of water soluble salts of other pesticide compounds did not lead to an increased storage stability. Therefore, the present invention also relates to the use of a glyphosate salt for increasing the storage stability of a flowable, aqueous concentrate composition containing 50 to 400 g/l of microcapsules comprising a core material containing a dinitroaniline herbicide and a polymeric wall material surrounding the core material, wherein microcapsules are dispersed in an aqueous phase. The increase in storage stability by the addition of the glyphosate salt allows to replace at least partly the inorganic salt, which is usually required to stabilize formulations of microencapsulated dinitroaniline herbicides. The inventors of the present invention believe that the increased storage stability of the compositions results from a reduction of the solubility of the dinitroaniline herbicide in the aqueous phase which is achieved by the addition of the glyphosate salt. The reduced solubility slows possible leaching of the dinitroaniline from the microcapsule followed by formation of crystalline material. However, other factors may also play a role.

In the context of the present invention, the term "flowable" means that the composition is liquid and can e.g. be poured or pumped. Usually, the composition has a viscosity, at 20° C., of at most 1000 mPa·s, e.g. from 10 to 1000 mPa·s, in particular from 15 to 600 mPas, determined according to ASTM D 2196 by means of a Brookfield viscosimeter.

In the context of the present invention, the term "microcapsule" means a particulate material, wherein the particles comprise a core material and which is surrounded by a polymeric wall material. According to the present invention, the core material contains at least one dinitroaniline herbicide and optionally further material, e.g. an oil and/or a further pesticide compound having a reduced water solubility, which generally does not exceed 10 g/l, in particular 5 g/l or even 1 g/l at 25° C. (deionised water).

The particle size of microcapsule particles will in general not exceed 40 μm and preferably 30 μm. The particle size given is the so called $D_{90}$-value, which has to be understood that at least 90% by weight of the particles having a diameter below said $D_{90}$ value. Preferably the microcapsule particles have an average particle size (weight average, also termed $D_{50}$ value) ranging from 0.5 to 20 µm, in particular from 1 to 10 µm. Preferably at least 90% by weight of microcapsule particles have diameters in the range from 0.5 to 20 µm, in particular in the range from 1 to 10 µm. The particle size of the microcapsule particles can be determined by conventional methods such as light-scattering.

Suitable dinitroanilines herbicides include benfluralin, butralin, dinitramine, ethalfluralin, fluchloralin, isopropalin, methalpropalin, nitralin, oryzalin pendimethalin, prodiamine, profluralin and trifluralin and mixtures thereof. The advantages of the present invention are pronounced, if the core material contains pendimethalin, i.e. the dinitroaniline herbicide is pendimethaline or a mixture thereof with one or more of the aforementioned dinitroaniline herbicides. In particular, pendimethaline is the only dinitroaniline herbicide contained in the microcapsules or in the composition or makes up at least 90% of the dinitroaniline herbicides contained in the microcapsules or in the composition.

The core material may further contain an oil, e.g. a hydrocarbon solvent such a an aromatic, paraffinic or isoparaffinic hydrocarbon, having preferably a boiling point above 100° C., a vegetable oil such as corn oil, rapeseed oil, or a fatty acid ester such as $C_1$-$C_{10}$-alkylester of a $C_{10}$-$C_{22}$-fatty acid, in particular methyl- or ethyl esters of vegetable oils such as rapeseed oil methyl ester or corn oil methyl ester. In a particular embodiment, the core material does not contain an oil as defined herein or less than 10% by weight, based on the weight of the core material, of an oil.

The core material may further contain a further pesticide compound, in particular a herbicide compound or a safener, having preferably a reduced water solubility, which generally does not exceed 10 g/l, in particular 5 g/l or even 1 g/l at 25° C. (de-ionised water). Suitable herbicides, which can be contained in the core material of the microcapsules include, e.g.
chloroacetamide herbicides, such as acetochlor, alachlor, butachlor, butenachlor, delachlor, diethatyl, dimethachlor, metolachlor, metolachlor-S, metazachlor, pretilachlor, propachlor, propisochlor, prynachlor, terbuchlor, thenylchlor, xylachlor, dimethenamid, dimethenamid-P,
oxyacetamide herbicides such as flufenacet and mefenacet,
acetamide herbicides, such as diphenamid, napropamide and naproanilide,
tetrazolinone herbicides, such as fentrazamide,
arylurea herbicides such as chlorbromuron, chlorotoluron, chloroxuron, dimefuron, diuron, ethidimuron, fenuron, fluometuron, isoproturon, isuron, linuron, methabenzthiazuron, metobromuron, metoxuron, monolinuron, neburon, siduron, tetrafluron and thebuthiuron,
triazine herbicides such as atrazine, chlorazine, cyanazine, cyprazine, eglinazine, ipazine, mesoprazine, procyazine, proglinazine, propazine, sebuthylazine, simazine, terbuthylazine and trietazine;
triazin(di)one herbicides such as ametridione, amibuzin, hexazinone, isomethiozin, metamitron and metribuzin,
phenylcarbamate herbicides such as desmedipham, phenisopham, phenmedipham and phenmedipham-ethyl,
nitrile herbicides such as bromobonil, bromoxynil, chloroxynil, dichlobenil, iodobonil and ioxynil,
methylthiotriazine herbicides such as ametryn, aziprotryne, cyanatryn, desmetryn, dimethametryn, methoprotryne, prometryn, simetryn and terbutryn,
pyridazinone herbicides, such as norflurazon, brompyrazon, chloridazon, dimidazon, metflurazon, norflurazon, oxapyrazon and pydanon,
pyridinecarboxamide herbicides, such as flufenican, diflufenican and picolinafen, beflubutamid, fluridone, flurochloridone and flurtamone,
4-HPPD inhibitors such as isoxaflutole, mesotrione, tembotrione, topramezone and sulcotrione,
pyridine herbicides such as dithiopyr or thiazopyr, and
herbicide safeners such as benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloracetyl)-1,3-oxazolidine, 4-(dichloroacetyl)-1-oxa-4-azaspiro[4.5]decane and oxabetrinil, as well as thereof agriculturally acceptable salts and, provided they have a carboxyl group, their agriculturally acceptable derivatives. 2,2,5-Trimethyl-3-(dichloroacetyl)-1,3-oxazolidine [CAS No. 52836-31-4] is also known under the name R-29148.4-(Dichloroacetyl)-1-oxa-4-azaspiro [4.5]decane [CAS No. 71526-07-03] is also known under the names AD-67 and MON 4660.

Preferred further pesticide compounds are those of the groups of chloroacetamide herbicides, oxyacetamide herbicides, and herbicide safeners.

In a particular preferred embodiment, the dinitroaniline herbicide, in particular pendimethalin, makes up at least 80%, in particular at least 90% of the core material. In another embodiment, the core material contains from 10 to 90% by weight, in particular from 30 to 80% by weight of at least one dinitroaniline, in particular pendimethaline, and from 10 to 90% by weight, in particular from 20 to 70% by weight of at least one further material which is selected from an oil and pesticide compounds having a reduced water solubility and mixtures thereof.

In microcapsules, the core material is encapsulated within a polymeric wall material, which is principally water-insoluble. Water insoluble means that the polymeric wall material does not dissolve in deionised water at 20° C. or has as solubility in deionised water of at most 0.1 g/l. Examples for suitable wall materials are polyamides, polysulfonamides, polyesters, polycarbonates, polyurethanes or polyureas. Preferred wall materials are polyurethanes and most preferred polyureas and mixtures thereof.

The amount of polymeric wall material in the microencapsule particles will generally not exceed 30% by weight of the microcapsule material (i.e. the sum of the core material and the polymeric wall material) in order to ensure that the actives are sufficiently released from the particles. On the other hand, the amount of polymeric wall material is generally at least 0.5% of the microcapsule material in order to ensure a sufficient encapsulation of the core material. Frequently, the amount of polymeric wall material in the microcapsule particles is in the range from 0.5 to 30% by weight, preferably from 1 to 20% by weight and especially preferred from 1.5 to 15% by weight, based on the total weight of the microcapsule particles.

Microcapsule particles useful for the compositions according to the invention can be prepared by analogy to prior art. They are preferably prepared by an interfacial polymerization process of a suitable polymer wall forming material. Interfacial polymerization is usually performed in an aqueous water-in-oil emulsion or suspension of the core material containing dissolved therein at least one part of the polymer wall forming material. During the polymerization, the polymer segregates from the core material to the boundary surface between the core material and water thereby forming the wall of the microcapsule. Thereby an aqueous suspension of the microcapsule material is obtained.

Suitable wall forming materials for interfacial polymerization include in particular 2- or 3-component systems such as
polyfunctional isocyanate/polyfunctional alcohol,
polyfunctional isocyanate/polyfunctional amine,
polyfunctional isocyanate+polyfunctional acid or acid chloride/polyfunctional amine,
polyfunctional acid or acid chloride/polyfunctional alcohol,
polyfunctional acid or acid chloride/polyfunctional amine,
polyfunctional sulfonic acid chloride/polyamine,
urea/formaldehyde,
melamine/formaldehyde and the like.

The term "polyfunctional" indicates that the respective component on an average has at least 2 functional groups per molecule. The microcapsules may also be prepared by coacervation techniques.

Preferred wall forming materials for interfacial polymerization include in particular 2- or 3-component systems such as
polyfunctional isocyanate/polyfunctional alcohol,
polyfunctional isocyanate/polyfunctional amine and
polyfunctional isocyanate+polyfunctional acid or acid chloride/polyfunctional amine.

Suitable methods for interfacial polymerization processes for preparing microcapsules containing pesticide compounds have been disclosed in prior art, e.g. U.S. Pat. No. 3,577,515, U.S. Pat. No. 4,280,833, U.S. Pat. No. 5,049,182, U.S. Pat. No. 5,229,122, U.S. Pat. No. 5,310,721, U.S. Pat. No. 5,705,174, U.S. Pat. No. 5,910,314, WO 95/13698, WO 00/10392, WO 01/68234, WO 03/099005, EP 619,073 or EP-A1 1,109,450, to which full reference is made.

In a very preferred embodiment of the present invention the polymeric wall material is a polyurea. In general, polyureas are formed by reacting a polyfunctional isocyanate (=polyisocyanate) having at least two isocyanate groups with a polyfunctional amine (=polyamine) having at least two primary amino groups, optionally in the presence of a polyfunctional acid chloride, to form a polyurea wall material. Polyfunctional isocyanates which are suitable for use include di- and triisocyanates, wherein the isocyanate groups are attached to an aliphatic or cycloaliphatic moiety (aliphatic isocyanates) or to an aromatic moiety (aromatic isocyanates). Examples of suitable aliphatic diisocyanates include tetramethylene diisocyanate, pentamethylene diisocyanate and hexamethylene diisocyanate as well as cycloaliphatic isocycantates such as isophoronediisocyanate, 1,4-bisisocyanatocyclohexane and bis-(4-isocyanatocyclohexyl)methane. Suitable aromatic isocyanates include toluene diisocyanates (TDI: a mixture of the 2,4- and 2,6-isomers), diphenylmethene-4,4'-diisocyanate (MDI: DESMODUR® VL, Bayer Corp., Pittsburgh), polymethylene polyphenyl isocyanate (MONDUR® MR, Bayer Corp., Pittsburgh), PAPI® and PAPI® 135 (Upjohn Co.), 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4',4''-triphenylmethane triisocyanate.

Also suitable are higher oligomers of the aforementioned diisocyanates such as the isocyanurates and biurethes of the aforementioned diisocyanates and mixtures thereof with the aforementioned diisocyanates.

Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol and mixtures thereof with the aforementioned diisocyanates. In this way, several molecules of diisocyanate are linked through urethane groups to the polyhydric alcohol to form high molecular weight polyisocyanates. A particularly suitable product of this kind, DESMODUR® L (Bayer Corp., Pittsburgh), can be prepared by reacting three moles of toluene diisocyanate with one mole of 2-ethylglycerol (1,1-bismethylolpropane). Further suitable products are obtained by addition of hexamethylene diisocyanate or isophorone diisocyanate with ethylene glycol or glycerol.

Preferred polyisocyanates are diphenylmethane-4,4'-diisocyanate and higher oligomers of diphenylmethane-4,4'-diisocyanate (polymethylene polyphenolisocyanate) which preferably have an average functionality ranging from 2.1 to 2.9 and a typical isocyanate equivalent weight of 127 to 150.

Di- and triisocyanates, such as those mentioned above can be employed individually or as mixtures of two or more such isocyanates.

Suitable polyfunctional amines within the scope of this invention will be understood as meaning in general those compounds that contain two and more primary amino groups in the molecule, which amino groups may be linked to aliphatic or aromatic moieties. Examples of suitable aliphatic polyamines are α,ω-diamines of the formula

$$H_2N-(CH_2)_n-NH_2$$

wherein n is an integer from 2 to 6. Exemplary of such diamines are ethylenediamine, propylene-1,3-diamine, tetramethylenediamine, pentamethylenediamine and hexamethylenediamine. A preferred diamine is hexamethylenediamine.

Further suitable aliphatic polyamines are polyethylenimines of the formula

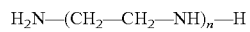

$$H_2N-(CH_2-CH_2-NH)_n-H$$

wherein n is an integer from 2 to 5. Representative examples of such polyethylenimines are diethylenetriamine, triethylenetetramine, tetraethylenepentamine and pentaethylenehexamine.

Further suitable aliphatic polyamines are dioxaalkane-α,ω-diamines, such as 4,9-dioxadodecane-1,12-diamine of the formula

$$H_2N-(CH_2)_3-O-(CH_2)_4-O-(CH_2)_3-NH_2.$$

Examples of suitable aromatic polyamines are 1,3-phenylenediamine, 2,4- and 2,6-toluenediamine, 4,4'-diaminodiphenylmethane, 1,5-diaminonaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole and 1,4,5,8-tetraaminoanthraquinone. Those polyamines which are insoluble or insufficiently soluble in water may be used as their hydrochloride salts.

Yet further suitable polyamines are those that contain sulfo ($SO_3H$) or carboxyl groups in addition to the amino groups. Examples of such polyamines are 1,4-phenylenediaminoesulfonic acid, 4,4'-diaminodiphenyl-2-sulfonic acid, or diaminomonocarboxylic acids, such as ornithine and lysine.

Polyamines, such as those mentioned above may be used individually or as mixtures of two or more polyamines.

The relative amounts of each complementary wall-forming component will vary with their equivalent weights. In general, approximately stoichiometric amounts are preferred, while an excess of one component may also be employed, especially an excess of polyisocyanate. The total amount of wall-forming components approximately corresponds to the total amount of polymeric wall-forming materials.

The compositions according to the invention usually contain the at least one microencapsulated dinitroaniline at a total concentration from 50 to 400 g/l, preferably of from 100 to 380 g/l and especially of from 150 to 350 g/l. The total concentration of microcapsule material (polymeric wall material+core material) will preferably be in the range form 100 to 420 g/l, preferably of from 150 to 400 g/l and especially of from 200 to 380 g/l.

The compositions according to the invention also contain at least one glyphosate salt. The total concentration of the glyphosate salt may range from 100 to 500 g/l, preferably of from 150 to 480 g/l and especially of from 200 to 450 g/l.

The total concentration of microcapsules, glyphosate salt and further active ingredients will be usually in the range from 150 to 820 g/l, in particular from 250 to 800 g/l, more preferably from 300 to 780 g/l.

The weight ratio of glyphosate salt, calculated as glyphosate, and dinitroaniline herbicides, will be usually from 1:1 to 10:1, preferably from 1.2:1 to 4:1, in particular from 1.5:1 to 3:1.

Preferably, the glyphosate salt is selected form glyphosate sodium, glyphosate ammonium, glyphosate potassium, glyphosate diglycolammonium and glyphosate isopropylamonium and mixtures thereof.

In particular, the glyphosate salt is selected from glyphosate sodium, glyphosate isopropylammonium and their mixtures.

The composition according to the invention further contains at least one surface-active substance (also termed surfactant). Surface-active substances comprise emulsifiers, protective colloids, wetting agents and dispersants that are normally employed in agricultural suspension concentrates and aqueous microcapsule formulations of pesticides. The surfactants may be nonionic, anionic and/or cationic. According to the present invention, the compositions of the present invention contain at least one anionic surfactant, optionally in combination with at least one nonionic surfactant. Suitable surfactants which may be used in the compositions of the invention are disclosed e. g. in "McCutcheon's Detergents and Emulsifiers Annual", MC Publishing Corp., Ridgewood, N.J., USA 1981; H. Stache, "Tensid-Taschenbuch", $2^{nd}$ ed., C. Hanser, Munich, Vienna, 1981; M. and J. Ash, "Encyclopedia of Surfactants", vol. I-III, Chemical Publishing Co., New York, N.Y., USA 1980-1981.

The total amount of anionic surfactant is preferably in the range from 0.2 to 10% by weight, in particular from 0.3 to 5% by weight, more preferably from 0.5 to 3% by weight, based on the microcapsules in the composition. The total concentration of the anionic surfactant in the composition is preferably from 1 to 45 g/l in particular from 2 to 40 g/l and most preferred from 3 to 30 g/l.

In a preferred embodiment of the invention, the composition contains at least one anionic oligomeric or polymeric surface-active substance A which contains a plurality of anionic groups, such as carboxylate groups, sulfonate groups, phosphonate groups, sulfate groups and/or phosphate groups. Preferably, the anionic groups are selected from sulfonate groups and carboxylate groups and are in particular sulfonate groups. The anionic groups in these oligomeric or polymeric compounds may be partially or fully neutralized. Suitable counter ions are sodium, potassium, magnesium, calcium and ammonium. Examples for oligomeric and polymeric substances A are the salts of ethoxylated lignosulfonic acid, of lignosulfonic acid, of oxidized lignins, the salts of styrenemaleic anhydride copolymers, the salts of homo-, co- and terpolymers of acrylic acid, the salts of arylsulfonic acid formaldehyde condensates and of arylsulfonic acid formaldehyde urea condensates, such as naphthalene sulfonic acid formaldehyde condensates, phenol sulfonic acid formaldehyde condensates, cresol sulfonic acid formaldehyde condensates etc.

The concentration of the surface-active substance A in the composition is preferably from 1 to 45 g/l in particular from 2 to 40 g/l and most preferred from 3 to 30 g/l.

A particular preferred embodiment of the invention relates to a composition, wherein the least one anionic surface-active substance A is an anionic oligomer or polymer, which contains a plurality of sulfonate groups. In particular, the anionic oligomer or polymer is selected from oxidized alkali-lignin, lignosulfonates, ligninsulfates, and the salts of arylsulfonic acid formaldehyde condensates and of arylsulfonic acid formaldehyde urea condensates and mixtures thereof.

Further anionic surfactants, which may be used instead or together with the oligomeric or polymeric surface-active substance A are anionic surface-active compounds B, which are selected of the groups of the salts, in particular the sodium, potassium or ammonium salts, of alkylsulfonates, alkylphosphates, semi-esters of alkoxylated alkanols with sulfuric acid or phosphoric acid, alkylarylsulfonates, alkylarylphosphates, semi-esters of alkoxylated alkylphenols with sulfuric acid or phosphoric acid and semi-esters of alkoxylated mono-, di- or tristyrylphenols with sulfuric acid or phosphoric acid and the formaldehyde condensation products of the latter. Amongst these anionic surfactants B, those of the formula I are preferred:

$$R\text{—}(O\text{-}A)_m\text{—}O\text{—}X \qquad\qquad I$$

wherein
R is a hydrocarbon radical having from 8 to 40 carbon atoms and preferably from 12 to 30 carbon atoms and optionally one oxygen atom;
A is independently from one another 1,2-ethylene, 1,2-propylene or 1,3-propylene, especially 1,2-ethylene;
m is from 3 to 200, preferably from 5 to 100 and especially preferred from 5 to 50; and
X is $SO_3M$ or $PO_3M_2$ with m being selected from H, alkaline metals, such as K and A, alkaline earth metals, such as Ca and Mg and ammonium. Preferably, M is an alkaline metal and especially sodium.

Examples of suitable hydrocarbon radicals R having from 8 to 40 carbon atoms are alkyl having from 8 to 40 and preferably from 12 to 30 carbon atoms, phenyl, which may be substituted with one or two alkyl radicals having from 4 to 20 carbon atoms, phenyl, which is substituted with a phenoxy radical, wherein phenyl and/or phenoxy may contain an alkyl radical having from 4 to 20 carbon atoms, tristyrylphenyl radical etc. In a preferred embodiment of the present invention the radical R in formula I is a tristyrylphenyl radical.

If present, the amount of anionic surfactant B, in particular the surface-active compound I, will be from 1 to 30% by weight, especially from 2 to 20% by weight and most preferred from 3 to 15% by weight, based on the total amount of water insoluble material, i.e. microcapsules and optionally further suspended pesticide material in the composition.

The compositions according to the invention may also contain a nonionic surface-active compound (nonionic surfactant). Preferred nonionic surfactants include the neutral surface-active compounds of the formula II, $$R'\text{—}(O\text{-}B)_n\text{—}OH \qquad\qquad II$$

wherein
R' is a hydrocarbon radical having from 8 to 40 and more preferably from 12 to 30 carbon atoms and optionally one oxygen atom, B is $C_2$-$C_4$-alkane-1,2-diyl such as 1,2-ethylene, 1,2-propylene or 1,2-butylene or a combination thereof and more preferred 1,2-ethylene or a combination thereof with 1,2-propylene, and n is from 3 to 100, preferably from 4 to 50 and more preferred from 5 to 40.

Examples of suitable hydrocarbon radials R' include the radicals mentioned for R. In a preferred embodiment of the invention the radical R' is a phenyl radical being substituted with one $C_4$-$C_{18}$-alkyl group.

If present, the concentration of nonionic surfactant, in particular the surface-active compound of the formula II, will be preferably from 5 to 150 g/l, in particular from 10 to 100 g/l of the composition. In one particular embodiment of the invention, the composition does not contain nonionic surfactant or less than 10 g/l of nonionic surfactant, in particular less than 5 g/l of nonionic surfactant.

Apart from the microencapsules, the glyphosate salt and the surface-active substance(s), the composition of the invention may also contain a water-soluble, inorganic salt which may result from the preparation of the microencapsules or which may be added thereafter. If present, the concentration of the water-soluble, inorganic salt may vary from 1 to 200 g/l, preferably from 2 to 150 g/l and especially from 10 to 100 g/l. In another particular embodiment, the composition does not contain or contains less than 10 g/l in particular less than 1 g/l of water-soluble, inorganic salt. Water-solubility means solubility in water of at least 50 g/l, in particular at least 100 g/l or even at least 200 g/l at 20° C. Such inorganic salts are preferably selected from sulfates, chlorides, nitrates, mono and dihydrogen phosphates of alkali metals, the sulfates, chlorides, nitrates, mono and dihydrogen phosphates of ammonia, chlorides and nitrates of alkaline earth metals and magnesium sulfate. Examples include lithium chloride, sodium chloride, potassium chloride, lithium nitrate, sodium nitrate, potassium nitrate, lithium sulfate, sodium sulfate, potassium sulfate, sodium monohydrogen phosphate, potassium monohydrogen phosphate, sodium dihydrogen phosphate, potassium dihydrogen phosphate, magnesium chloride, calcium chloride, magnesium nitrate, calcium nitrate, magnesium sulfate, ammonium chloride, ammonium sulfate, ammonium monohydrogen phosphate, ammonium dihydrogen phosphate and the like. Preferred salts are sodium chloride, potassium chloride, calcium chloride, ammonium sulfate and magnesium sulfate with ammonium sulfate and magnesium sulfate being especially preferred.

In a particular embodiment of the invention, the composition additionally contains a salt of a herbicide compound which is dissolved in the aqueous phase and which is different from the glyphosate salt. In this embodiment, the salt of the herbicide compound is usually present in an amount of from 1 to 200 g/l, in particular from 10 to 150 g/l. The total concentration of glyphosate salt and further herbicide salt will generally not exceed 550 g/l, and will be preferably from 110 to 550 g/l, preferably of from 160 to 500 g/l and especially of from 210 to 480 g/l.

Suitable herbicide salts include but are not limited to:
salts of glufosinate such as glufosinate ammonium;
salts of fosamine such as fosamine ammonium;
salts of imidazolinone herbicides such as imazapic, imazamox, imazapyr, imazaquin, or imazethapyr, in particular the sodium or ammonium salts such as imazamox-ammonium, imazapic-ammonium, imazapyr-isopropylammonium, imazaquin-ammonium, imazaquin-sodium and imazethapyr-ammonium;

salts of pyrimidinylcarboxylate herbicides such as pyrithiobac, bispyribac, pyriminobac, pyribenzoxim or pyriftalid, in particular their sodium salts;

salts of benzoic acid herbicides such as dicamba, tricamba, chloramben and 2,3,6-TBA (2,3,6-trichlorobenzoic acid), in particular the sodium, potassium, ammonium salts or substituted ammonium salts such as methylammonium, dimethylammonium and isopropylammonium, mono-, di- and tri-hydroxy-$C_2$-$C_8$-alkylammonium salts such as hydroxyethylammonium, di(hydroxylethyl)ammonium, tri(hydroxyethyl)ammonium, hydroxypropylammonium, di(hydroxypropyl)ammonium and tri(hydroxypropyl)ammonium salts;

salts of phenoxycarboxylic acids, e.g. the salts of phenoxyacetic acid herbicides such as 2,4-D, 3,4-DA, MCPA, 2,4,5-T, the salts of phenoxypropionic acid herbicides such as 2,4-DP (dichlorprop), 2,4-DP-P, 4-CPP, 3,4-DP, fenoprop, CMPP (mecoprop), CMPP-P, and the salts of phenoxybutyric acid herbicides such as 4-CPB, 2,4-DB, 3,4-DB, 2,4,5-TB, MCPB, in particular the sodium, potassium, ammonium salts or substituted ammonium salts such as methylammonium, dimethylammonium and isopropylammonium, mono-, di- and tri-hydroxy-$C_2$-$C_8$-alkylammonium salts such as hydroxyethylammonium, di(hydroxylethyl)ammonium, tri(hydroxyethyl)ammonium, hydroxypropylammonium, di(hydroxypropyl)ammonium and tri(hydroxypropyl) ammonium salts;

salts of pyridinecarboxylic acids, such as aminopyralid, clopyralid, picloram, triclopyr or fluroxypyr, in particular their sodium salt, potassium salt, ammonium salt or substituted ammonium salts as defined above, and salts of quinolinecarboxylic acids, such as quinclorac or quinmerac, in particular their sodium salt, potassium salt, ammonium salt or substituted ammonium salts as defined above.

In another embodiment, the composition does not contain dissolved in the aqueous phase a salt of a herbicide compound different from the glyphosate salt.

In a particular embodiment of the invention, the composition additionally contains a further non-encapsulated water-insoluble pesticide compound which is suspended in the aqueous phase. In this context, the term water-insoluble means that the solubility in water of the respective pesticide compound does not exceed 10 g/l, particular 5 g/l or even 1 g/l at 25° C. The water-insoluble pesticide may be present in the form of particle or in the form of microcapsules. The water-insoluble pesticide is preferably a herbicide compound, in particular a herbicide selected from the group of dinitroaniline herbicides, chloroacetamide herbicides, oxyacetamide herbicides, acetamide herbicides, tetrazolinone herbicides, arylurea herbicides, triazine herbicides, triazin(di)one herbicides, phenylcarbamate herbicides, nitrile herbicides, methylthiotriazine, pyridazinone herbicides, pyridinecarboxamide herbicides, 4-HPPD inhibitors and pyridine herbicides, or a herbicide safener.

The particle size of the further pesticide particles will in general not exceed 40 μm and preferably 30 μm ($D_{90}$-value). Preferably, the particles of the suspended further pesticide have an average particle size (weight average, $D_{50}$ value) ranging from 0.5 to 20 μm, in particular from 1 to 10 μm. Preferably at least 90% by weight of the particles of the further pesticide have diameters in the range from 0.5 to 20 μm, in particular in the range from 1 to 10 μm.

The further pesticide compound which is suspended in the aqueous phase is usually present in an amount of from 1 to 200 g/l, in particular from 10 to 150 g/l. The total amount of microcapsules and further pesticide compound will generally not exceed 550 g/l, and will be preferably from 55 to 520 g/l, preferably of from 110 to 500 g/l and especially of from 170 to 450 g/l.

In another embodiment, the composition does not contain a further non-encapsulated water-insoluble pesticide compound which is suspended in the aqueous phase.

The composition of the invention may further contain customary auxiliaries, such as defoamers, thickeners, anti-freezes, preservatives, anti-settling agents etc. which are usually employed in aqueous formulations of pesticides.

Suitable thickening agents include inorganic thickening agents, such as clays, hydrated magnesium silicates and organic thickening agents, such as polysaccharide gums, like xanthan gum, guar gum, gum arabic and cellulose derivatives. Organic thickening agents are usually contained in amounts of from 0.5 to 30 g/l and preferably from 1 to 10 g/l while inorganic thickening agents are usually contained in amounts of from 0.5 to 30 g/l and preferably from 1 to 10 g/l.

Suitable preservatives to prevent microbial spoiling of the compositions of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof. In general, the amount of preservatives will be from 0.1 to 10 g/l.

Suitable anti-freezing agents include organic solvents which are completely miscible with water, such as ethylene glycol, propylene glycol, other glycols, glycerin or urea.

The compositions of the invention can be easily obtained by mixing the first flowable, aqueous composition containing particles of microencapsulated dinitroaniline herbicide with the glyphosate salt or with and aqueous composition containing the glyphosate salt. Preferably, the compositions according to the present invention are prepared by a process comprising:
  i) providing an aqueous suspension of microcapsules comprising a core material containing a dinitroaniline herbicide and a polymeric wall material surrounding the core material, the microcapsules being dispersed in an aqueous phase of the suspension; and
  ii) dissolving the glyphosate salt in the aqueous suspension of the microcapsules.

Methods for providing aqueous suspensions of microcapsules are known in the art and have been explained above. In particular the aqueous suspensions of the microcapsules are provided by an interfacial polymerization process in an aqueous suspension or emulsion of the material to be encapsulated by a so-called interfacial polymerization process. Suitable methods for interfacial polymerization processes for preparing microcapsules containing pesticide compounds have been disclosed in prior art, e.g. U.S. Pat. No. 3,577,515, U.S. Pat. No. 4,280,833, U.S. Pat. No. 5,049,182, U.S. Pat. No. 5,229,122, U.S. Pat. No. 5,310,721, U.S. Pat. No. 5,705,174, U.S. Pat. No. 5,910,314, WO 95/13698, WO 00/10392, WO 01/68234, WO 03/099005, EP 619,073 or EP-A1 1,109,450, to which full reference is made.

If the composition contains further actives, they will be generally incorporated in the composition in a similar manner, e.g. simply by mixing the first flowable, aqueous composition containing the microcapsules with an aqueous composition of the further pesticide compound and with the glyphosate salt or an aqueous composition thereof. Further auxiliaries will be incorporated into the composition in a similar manner.

The mixing of the first and further compositions can be achieved by conventional means for mixing aqueous suspensions with further ingredients. The temperature at which mixing is performed is not critical and may in general vary from 0 to 60° C., especially from 10 to 50° C. or 20 to 35° C.

The compositions according to the invention are useful for controlling undesirable plants. Due to their higher storage stability, especially at temperature exceeding 30° C., especially at 35° C. or higher and even at temperatures exceeding 45° C. the compositions are easy to handle. Advantageously the compositions of the invention show a superior activity towards undesirable plants in comparison with conventional formulations of dinitroaniline herbicides or formulations of microencapsulated dinitroaniline herbicides. Consequently the compositions are easier to handle than conventional concentrate compositions of dinitroaniline herbicides. Thus, the present application also relates to the use of the compositions for controlling undesired vegetation.

The compositions of the present invention are suitable for controlling a large number of harmful plants, including monocotyledonous weeds, in particular annual weeds such as gramineous weeds (grasses) including *Echinochloa* species such as barnyard grass (*Echinochloa crusgalli* var. *crusgalli*), *Digitaria* species such as crabgrass (*Digitaria sanguinalis*), *Setaria* species such as green foxtail (*Setaria viridis*) and giant foxtail (*Setaria faberii*), *Sorghum* species such as johnsongrass (*Sorghum halepense* Pers.), *Avena* species such as wild oats (*Avena fatua*), *Cenchrus* species such as *Cenchrus echinatus*, *Bromus* species, *Lolium* species, *Phalaris* species, *Eriochloa* species, *Panicum* species, *Brachiaria* species, annual bluegrass (*Poa annua*), blackgrass (*Alopecurus myosuroides*), *Aegilops cylindrica*, *Agropyron repens*, *Apera spica-venti*, *Eleusine indica*, *Cynodon dactylon* and the like.

The compositions of the present invention are also suitable for controlling a large number of dicotyledonous weeds, in particular broad leaf weeds including *Polygonum* species such as wild buckwheat (*Polygonum convolvolus*), *Amaranthus* species such as pigweed (*Amaranthus retroflexus*), *Chenopodium* species such as common lambsquarters (*Chenopodium album* L.), *Sida* species such as prickly *sida* (*Sida spinosa* L.), *Ambrosia* species such as common ragweed (*Ambrosia artemisiifolia*), *Acanthospermum* species, *Anthemis* species, *Atriplex* species, *Cirsium* species, *Convolvulus* species, *Conyza* species, *Cassia* species, *Commelina* species, *Datura* species, *Euphorbia* species, *Geranium* species, *Galinsoga* species, morningglory (*Ipomoea* species), *Lamium* species, *Malva* species, *Matricaria* species, *Sysimbrium* species, *Solanum* species, *Xanthium* species, *Veronica* species, *Viola* species, common chickweed (*Stellaria media*), velvetleaf (*Abutilon theophrasti*), Hemp sesbania (*Sesbania exaltata* Cory), *Anoda cristata*, *Bidens pilosa*, *Brassica kaber*, *Capsella bursa-pastoris*, *Centaurea cyanus*, *Galeopsis tetrahit*, *Galium aparine*, *Helianthus annuus*, *Desmodium tortuosum*, *Kochia scoparia*, *Mercurialis annua*, *Myosotis arvensis*, *Papaver rhoeas*, *Raphanus raphanistrum*, *Salsola kali*, *Sinapis arvensis*, *Sonchus arvensis*, *Thlaspi arvense*, *Tagetes minuta*, *Richardia brasiliensis*, and the like.

The compositions of the present invention are also suitable for controlling a large number of annual and perennial sedge weeds including *cyperus* species such as purple nutsedge (*Cyperus rotundus* L.), yellow nutsedge (*Cyperus esculentus* L.), hime-kugu (*Cyperus brevifolius* H.), sedge weed (*Cyperus microiria* Steud), rice flatsedge (*Cyperus iria* L.), and the like.

The compositions according to the present invention are suitable for combating/controlling common harmful plants in useful plants (i.e. in crops). The compositions of the present invention are generally suitable for combating/controlling undesired vegetation in Grain crops, including e.g.
cereals such as wheat (*Triticum aestivum*) and wheat like crops such as durum (*T. durum*), einkorn (*T. monococcum*), emmer (*T. dicoccon*) and spelt (*T. spelta*), rye (*Secale cereale*), triticale (*Tritiosecale*), barley (*Hordeum vulgare*);
maize (corn; *Zea mays*);
sorghum (e.g. *Sorghum bicolour*);
rice (*Oryza* spp. such as *Oryza sativa* and *Oryza glaberrima*); and
sugar cane;

Legumes (Fabaceae), including e.g. soybeans (*Glycine max.*), peanuts (*Arachis hypogaea* and pulse crops such as peas including *Pisum sativum*, pigeon pea and cowpea, beans including broad beans (*Vicia faba*), *Vigna* spp., and *Phaseolus* spp. and lentils (*lens culinaris* var.);
brassicaceae, including e.g. canola (*Brassica napus*), oilseed rape (*Brassica napus*), cabbage (*B. oleracea* var.), mustard such as *B. juncea, B. campestris, B. narinosa, B. nigra* and *B. tournefortii*; and turnip (*Brassica rapa* var.);
other broadleaf crops including e.g. sunflower, cotton, flax, linseed, sugarbeet, potato and tomato;
TNV-crops (TNV: trees, nuts and vine) including e.g. grapes, citrus, pomefruit, e.g. apple and pear, coffee, pistachio and oilpalm, stonefruit, e.g. peach, almond, walnut, olive, cherry, plum and apricot;
turf, pasture and rangeland;
onion and garlic;
bulb ornamentals such as tulips and narcissus;
conifers and deciduous trees such as pinus, fir, oak, maple, dogwood, hawthorne, crabapple, and *rhamnus* (buckthorn); and
garden ornamentals such as petunia, marigold, roses and snapdragon.

The compositions according to the present invention can be easily diluted with water to the desired application concentration which is familiar. Thus obtained diluted compositions are ready to use and therefore usually referred to application form or as a tank-mix. The tank-mix obtained by diluting the compositions of the invention with can be applied before (preemergence), during and/or after the emergence of undesired plants (postemergence). Therefore the invention also relates to a method for controlling undesired vegetation, which comprises applying an aqueous tank-mix, which is obtained by diluting a composition according to the invention with water, before, during and/or after the emergence of undesired plants.

The amount of water being used to dilute the concentrate composition of the invention will usually be from 10 to 10000 times the volume of the concentrate composition.

The tank-mix can also be applied together with the seed of a crop plant. There is also the possibility of applying the compositions of the invention by applying seed of a crop plant pretreated with a diluted application form of the compositions of the invention. Preferably the compositions according to the invention are applied to the leaves of the undesired plants. Especially the diluted composition is applied in a manner such that the leaves of the crop plants are, wherever possible, not sprayed, while the composition reaches the leaves of the undesired (target) plants growing below or the exposed soil surface (post-directed or lay-by application). The application rates which are necessary to achieve the desired control are similar to those application rates required when using a conventional suspension concentrate of a dinitroaniline herbicide.

The examples below illustrate the present invention:

I. PREPARATION EXAMPLES

I.1 Preparation of a Pendimethalin Microcapsules Stock Suspension

Reference Example R1

An aqueous stock solution of water (553.9 g), 40% solution of sodium lignin sulfonate (43.8 g), antifoam (0.9 g) and biocide (1.5 g) was prepared. A mixture of pendimethalin (926.6 g) was heated to 65° C., and 29.9 g of a polyisocyanate based on 4,4'diisocyanatodiphenylethane having an equivalent weight of 133 and an NCO-content of 31.1% (Mondur® MRS of Bayer Materialscience) was then added to 535.7 g of the above aqueous stock solution. The mixture was heated to 65° C., and stirred to form an emulsion. A solution of 1,6-hexamethylenediamine (HMDA, 10.4 g) in water (31.2 g) was then added and the mixture was stirred for about 1 hour to from microcapsules. 66.5 g of an aqueous solution of the suspending aid, consisting of 62.6 g of water, 0.26 g of a thickener, 1.31 g of a biocide and 1.31 g of the suspending aid, was then added and mixed until uniform. The obtained composition has the following overall composition:

| | |
|---|---|
| Pendimethalin | 57.90% w/w |
| Wall material: | 2.52% w/w* |
| sodium lignin sulfonate: | 0.98% w/w |
| suspending aid: | 0.08% w/w |
| thickener: | 0.05% w/w |
| biocide: | 0.08% w/w |
| antifoam | 0.02% w/w |
| water: | 38.37% w/w |

*100% conversion assumed

Suspending aid: Sodium salt of a naphthalenesulfonic acid formaldehyde condensation product (e.g. Morwet D-425 of BASF SE)
Thickener: Xanthan gum
Antifoam: silicone based emulsion
Biocide: 5% aqueous composition of a 1:1 mixture of 2-methylisothiazol-3-one and 1,2-benzisothiazol-3-one (Acticide MBS)

Example 1 and Comparative Examples C2 to C8

Preparation of a Composition Containing Pendimethalin Microcapsules and Water Soluble Herbicide Salt (General Procedure)

The stock-suspension of reference example R1 was divided into 8 subsamples à 150 g. Each subsample was mixed with 100 g of one of the following aqueous solutions of herbicide salts until uniform.

| Example No. | Solution |
|---|---|
| 1 | Glyphosate IPA salt (45.8% w/w ae)** |
| C2* | Water |
| C3* | Dicamba DGA Salt Solution (38.5% w/w ae)** |
| C4* | Dicamba DMA Salt Solution (40% w/w ae)** |

-continued

| Example No. | Solution |
|---|---|
| C5* | 2,4 D Ammonium Salt Solution (46.8% w/w ae)** |
| C6* | Quinclorac DMA Salt Solution (15.9% w/w ae)** |
| C7* | Imazapyr IPA Salt Solution (42.9% w/w ae)** |
| C8* | Imazethapyr IPA Salt Solution (19.4% w/w ae)** |

*Comparative example
**Concentration of the herbicide, calculated as free acid
IPA: Isopropylammonium;
DGA: Diglycolammonium;
DMA: Dimethylammonium Each of the thus obtained formulations was divided into 3 subsamples and placed in storage stability test for one month at 40° C., 50° C. and through six (6) cycles of freeze-thaw and then examined for physical properties of the formulation including separation, settling out, tendency and leaching of pendimethalin for the capsules into the continuous phase as determined by free pendimethalin (e.g. by HPLC or UV/VIS). The results are summarized in table 1.

TABLE 1

| Example | 1 | C2 | C3 | C4 |
|---|---|---|---|---|
| 1 Month storage at 40° C. | | | | |
| Separation | None | 46% | 1% | 3% |
| Settling Out | None | Yes | Yes-Slight | Yes |
| Tendency to Gel | None | Yes-heavy | None | Moderate |
| Free Pendimethalin | 0.025 | 0.262 | 2.410 | 3.009 |
| 1 Month storage at 50° C. | | | | |
| Separation | None | 47% | 1% | 12% |
| Settling Out | None | Yes | None | Yes |
| Tendency to Gel | None | Yes-heavy | None | Slight |
| Free Pendimethalin | 0.019 | 0.157 | 3.098 | 3.097 |
| 6 cycles Freeze-Thaw | | | | |
| Separation | None | 19% | 20% | 3% |
| Settling Out | None | Yes | Yes | Yes |
| Tendency to Gel | None | None | V. Slight | Slight |
| Free Pendimethalin | 0.022 | 0.184 | 1.993 | 2.356 |

| Example | C5 | C6 | C7 | C8 |
|---|---|---|---|---|
| 1 Month storage at 40° C. | | | | |
| Separation | 13% | 40% | 28% | 43% |
| Settling Out | Yes | Yes | Yes | Yes |
| Tendency to Gel | Slight to Moderate | Heavy | Slight to Moderate | Moderate |
| Free Pendimethalin | 3.029 | 2.650 | 0.479 | 0.776 |
| 1 Month storage at 50° C. | | | | |
| Separation | 20% | 43% | 23% | 43% |
| Settling Out | Yes | Yes | Yes | Yes |
| Tendency to Gel | Slight | Heavy | Moderate | Heavy |
| Free Pendimethalin | 3.111 | 2.393 | 0.499 | 0.711 |
| 6 cycles Freeze-Thaw | | | | |
| Separation | 32% | 32% | 16% | 31% |
| Settling Out | Yes | Yes | Yes | Yes |
| Tendency to Gel | Heavy | Moderate | Moderate | Heavy |
| Free Pendimethalin | 3.078 | 0.546 | 0.068 | 0.302 |

The formulations of Comparative Examples C2, C3, C4, C5, C6, C7 and C8 failed for having poor stability and showing noticeable leaching of pendimethalin from the capsules into the aqueous phase. Surprisingly, Comparative example 2 shows less leaching than Comparative Examples C3 to C8. In contrast thereto, Example 1 according to the present invention did not show significant leaching and had good storage stability Reference Examples R2 to R10

Solubility Study of Pendimethalin in Glyphosate Salt Solutions

In support of the above storage stability study the solubility of pendimethalin in commercial glyphosate salt solutions was compared to water, and to a 15% water solution of $MgSO_4$ to predict the ability of the herbicide salt solution to lower the solubility of pendimethalin in the aqueous continuous phase.

Glyphosate salt solutions as isopropylamine, potassium, ammonium and sodium salt were prepared at different concentrations as shown in the following table. To 20 grams of each glyphosate salt solution 2 grams of Pendimethalin (technical grade) were added. Each sample was placed at 65° C. and allowed to come to equilibrium to completely saturate the solution with pendimethalin. The samples were then removed and placed in storage at 25° C. and allowed to come to equilibrium. After 3 days at 25° C. each solution was filtered through a 0.45 µm GMF filter and evaluated for pendimethalin dissolved in the aqueous phase and compared to water and a 15% water solution of $MgSO_4$ as controls.

TABLE 2

| Example | Water Soluble Salt Solution | Pendimethalin (ppm) |
|---|---|---|
| R2 | Water-Control | 9.4 |
| R3 | 15 w/w % $MgSO_4$ Solution | 4.8 |
| R4 | 40 w/w % Glyphosate IPA Salt | 4.6 |
| R5 | 30 w/w % Glyphosate IPA Salt | 4.5 |
| R5 | 20 w/w % Glyphosate IPA Salt | 3.3 |
| R6 | 40 w/w % Glyphosate Potassium Salt | 3.1 |
| R7 | 30 w/w % Glyphosate Potassium Salt | 3.1 |
| R8 | 20 w/w % Glyphosate Potassium Salt | 3.7 |
| R9 | 30 w/w % Glyphosate Ammonium Salt | 2.28 |
| R10 | 30 w/w % Glyphosate Sodium Salt | 0.684 |

Glyphosate IPA salt solutions showed reduction in solubility of pendimethalin equivalent or better than 15% $MgSO_4$ solution. Additionally, glyphate salt solutions of potassium, ammonium and sodium were better than glyphosate IPA salt solutions in reducing pendimethalin solubility in the aqueous phase. Thus, other glyphosate salts will also prevent pendimethalin from leaching from the microcapsules.

Example 9

An aqueous pendimethalin microcapsules stock suspension was prepared similar to the procedure described for reference example 1. The suspension was then blended with an aqueous 62% w/w concentrate solution of glyphosate isopropylammonium. The obtained composition has the following overall composition:

| | |
|---|---|
| Pendimethalin | 33.00% w/w |
| Wall material: | 1.68% w/w* |
| sodium lignin sulfonate: | 0.58% w/w |
| suspending aid: | 0.02% w/w |
| thickener: | 0.01% w/w |
| biocide: | 0.01% w/w |
| antifoam | 0.03% w/w |

| | |
|---|---|
| glyphosate IPA | 40.00% w/w |
| water: | 24.67% w/w |

*100% conversion assumed

The composition showed good physical and chemical stability under storage conditions of freeze-thaw and at 40° C. and 50° C. No significant leaching of pendimethalin was observed under storage conditions.

We claim:

1. A stable flowable aqueous concentrate composition containing
    i. about 100 to 400 g/l of pendimethalin in the form of microcapsules comprising a core material, which contains the pendimethalin, and a polymeric wall material, the microcapsules being dispersed in an aqueous phase;
    ii. 100 to 500 g/l of a glyphosate salt which is dissolved in the aqueous phase and
    iii. at least one anionic oligomer or polymer, wherein the anionic oligomer or polymer is selected from oxidized alkali-lignin, lignosulfonates, ligninsulfates, and the salts of arylsulfonic acid formaldehyde condensates and of arylsulfonic acid formaldehyde urea condensates and mixtures thereof.

2. The composition of claim 1, wherein the glyphosate salt is selected from the group consisting of glyphosate sodium, glyphosate ammonium, glyphosate potassium, glyphosate diglycolammonium and glyphosate isopropylammonium and mixtures thereof.

3. The composition of claim 2, wherein the glyphosate salt is selected from the group consisting of glyphosate sodium, glyphosate isopropylammonium and their mixtures.

4. The composition of claim 1, wherein the polymeric wall material is selected from the group consisting of polyamides, a polycarbonates, aminoresins, polysulfonamides, polyureas and polyurethanes and mixtures thereof.

5. The composition of claim 1, wherein the polymeric wall material amounts to 0.5 to 30% by weight, based on the amount of microcapsules.

6. The composition of claim 1, wherein the microcapsules have a volume average diameter in the range of 1 to 10 μm.

7. The composition of claim 1, wherein the total amount of the anionic oligomer or polymer is from 0.1 to 10% by weight, based on the microcapsules in the composition.

8. The composition of claim 1 further comprising at least one neutral surface-active compound, which is selected from polyethylenoxide-co-poly($C_3$-$C_4$-alkyleneoxide) blockpolymers and compounds of the formula I $$R'—(O-B)_n-OH \quad (I)$$

wherein

R' is a hydrocarbon radical having from 8 to 40 carbon atoms and optionally one oxygen atom, B is $C_2$-$C_4$-alkane-1,2-diyl and n is from 3 to 100.

9. The composition of claim 1 further comprising an inorganic water-soluble salt which is dissolved in the aqueous phase.

10. The composition of claim 9, wherein the inorganic salt is present in an amount of from 0.1 to 200 g/l.

11. The composition of claim 9, wherein the inorganic salt is selected from the group consisting of sulfates, chlorides, nitrates, mono and dihydrogen phosphates of alkali metals, sulfates, chlorides, nitrates, mono and dihydrogen phosphates of ammonia, chlorides and nitrates of alkaline earth metals and magnesium sulfate.

12. The composition of claim 10, wherein the inorganic salt is selected from the group consisting of sulfates, chlorides, nitrates, mono and dihydrogen phosphates of alkali metals, sulfates, chlorides, nitrates, mono and dihydrogen phosphates of ammonia, chlorides and nitrates of alkaline earth metals and magnesium sulfate.

13. The composition of claim 11, wherein the inorganic salt is selected from the group consisting of sodium chloride, potassium chloride, calcium chloride, magnesium sulfate and ammonium sulfate.

14. The composition of claim 1 which additionally contains a salt of a herbicide compound which is dissolved in the aqueous phase and which is different from the glyphosate salt.

15. The composition of claim 14, wherein the salt of the herbicide compound is present in an amount of from 1 to 200 g/l.

16. The composition of claim 1 wherein the microcapsules in addition to the pendimethalin contain at least one further active compound selected from herbicides and safeners.

17. The composition of claim 16, wherein the at least one further active compound has a water solubility of not more than 10 g/l at 25° C.

18. The composition of claim 16, wherein the at least one further active compound and the pendimethalin are present in the microcapsules in a weight ratio of from 1:9 to 9:1.

19. A method for controlling undesired vegetation, which comprises applying to seed, undesirable vegetation or soil surface an aqueous tank-mix, which is obtained by diluting a composition of claim 1 with water, before, during and/or after the emergence of undesired plants.

20. A process for preparing a flowable, aqueous concentrate composition of claim 1, which comprises:
    i) providing an aqueous suspension of microcapsules comprising a core material containing the pendimethalin and a polymeric wall material surrounding the core material, the microcapsules being dispersed in an aqueous phase of the suspension; and
    ii) dissolving the glyphosate salt in the aqueous suspension of the microcapsules.

21. A method for increasing the storage stability of a flowable, aqueous concentrate composition comprising dispersing microcapsules containing 50 to 400 g/l of microcapsules comprising
    i. about 100 to 400 g/l of pendimethalin in the form of microcapsules comprising a core material, which contains the pendimethalin, and a polymeric wall material, the microcapsules being dispersed in an aqueous phase;
    ii. 100 to 500 g/l of a glyphosate salt which is dissolved in the aqueous phase and
    iii. at least one anionic oligomer or polymer, wherein the anionic oligomer or polymer is selected from oxidized alkali-lignin, lignosulfonates, ligninsulfates, and the salts of arylsulfonic acid formaldehyde condensates and of arylsulfonic acid formaldehyde urea condensates and mixtures thereof.

* * * * *